United States Patent [19]
Kourai et al.

[11] Patent Number: 5,476,913
[45] Date of Patent: Dec. 19, 1995

[54] POLYMERIZABLE MONOMER, POLYMER THEREOF AND PROCESS FOR PREPARING SAME

[75] Inventors: Hiroki Kourai; Michio Sasaoka; Mitsuo Akada; Yoshio Yabuhara; Kouji Mori; Akihiro Murakami; Hiroshi Hama, all of Tokushima, Japan

[73] Assignee: Otsuka Kagaku Kabushiki Kaisha, Osaka, Japan

[21] Appl. No.: 204,210

[22] PCT Filed: Jul. 6, 1993

[86] PCT No.: PCT/JP93/00924

§ 371 Date: Jul. 11, 1994

§ 102(e) Date: Jul. 11, 1994

[87] PCT Pub. No.: WO94/01474

PCT Pub. Date: Jan. 20, 1994

[30] Foreign Application Priority Data

| Jul. 6, 1992 | [JP] | Japan | 4-203027 |
| Aug. 4, 1992 | [JP] | Japan | 4-229177 |
| Aug. 31, 1992 | [JP] | Japan | 4-257284 |
| Sep. 4, 1992 | [JP] | Japan | 4-262867 |

[51] Int. Cl.⁶ .............. C08F 220/56; C08F 226/02; C08F 216/36
[52] U.S. Cl. .............. 526/310; 526/312; 526/316; 526/332
[58] Field of Search ............... 526/310, 312, 526/316, 332

[56] References Cited

U.S. PATENT DOCUMENTS

| 3,825,511 | 7/1974 | Markhart et al. | 526/310 |
| 4,009,201 | 2/1977 | Steckler et al. | 260/486 |
| 4,826,924 | 5/1989 | Kourai et al. | 525/331.3 |

FOREIGN PATENT DOCUMENTS

| 0099694 | 2/1984 | European Pat. Off. |
| 55-11523 | 1/1980 | Japan |
| 61-100254 | 5/1986 | Japan |
| 61-246205 | 11/1986 | Japan |
| 2-64167 | 3/1990 | Japan |
| 4-342504 | 11/1992 | Japan |

OTHER PUBLICATIONS

Senuma et al., "Synthesis and Antibacterial Activities of Copolymers Having A Quaternary Ammonium Salt Group", High–Polymer Fiber Material Research Institute, Research Report, No. 159 (1988), pp. 17–22.

Primary Examiner—Joseph L. Schofer
Assistant Examiner—Wu C. Cheng
Attorney, Agent, or Firm—Ronald J. Kubovcik

[57] ABSTRACT

The present invention provides a polymerizable monomer represented by the general formula (1), polymer thereof, process for preparing the polymer and the use of the polymer

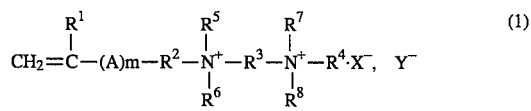

wherein $R^1$ is a hydrogen atom, methyl, chlorine or cyano, $R^2$ is alkylene having 1 to 4 carbon atoms, $R^3$ is alkylene having 3 to 10 carbon atoms, $R^4$ is alkyl having 6 to 18 carbon atoms, $R^6$ to $R^8$ are the same or different and are each alkyl or substituted alkyl having 1 to 3 carbon atoms, A is methylene, phenylene, substituted phenylene, $-CH_2O-$, $-CH_2CH_2O-$, $-CO-$, $-CO-N(R^9)-$ (wherein $R^9$ is a hydrogen atom or methyl) or vinylene, m is 0 or 1, and X and Y are the same or different, and are each a monovalent anion or form a bivalent anion when taken together.

5 Claims, No Drawings

POLYMERIZABLE MONOMER, POLYMER THEREOF AND PROCESS FOR PREPARING SAME

TECHNICAL FIELD

The present invention relates to polymerizable monomer, polymers thereof, process for preparing the polymer and the use of the polymer. The invention provides polymerizable monomers for readily giving antibacterial polymers which are excellent in bactericidal activity, high in safety and stability and capable of retaining their effect over a prolonged period of time, and also provides these polymers, process for preparing the same and the use of the same.

The antibacterial polymers derived from the polymerizable monomers of the invention are usable, for example, for sterilization or slime control of tap water, cooling water and water in pools, for compositions for preventing soiling of fishing nets, ship bottoms, underwater structures, etc., for food packaging materials, building materials, agricultural materials, medical articles, materials or utensils for use in the oral cavity (toothbrushes, toothpastes, etc.), spectacle frames, cosmetics, clothes, household utensils and the like, and a wide variety of other uses.

BACKGROUND ART

Among the conventional antibacterial compounds, those of low molecular weight are used as merely mixed with materials (such as resins) for forming various products, so that the antibacterial compound inevitably dissolves out, consequently becoming impaired in antibacterial activity and causing environmental pollution. Also encountered are problems such as toxicity of the compound to the living body due to contact with the product, and appearance of resistant bacteria.

To solve these problems, antibacterial polymers have been developed in recent years which are prepared by introducing an antibacterial functional group into high-molecular-weight compounds. These antibacterial polymers include, for example, those comprising a repeating unit represented by the general formula (3) (JP-A-100254/1986) and those comprising a repeating unit represented by the general formula (4) (JP-A-246205/1986).

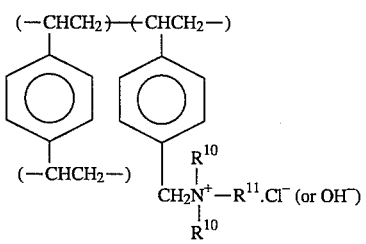

wherein $R^{10}$ is methyl or ethyl, $R^{11}$ is alkyl having 3 to 30 carbon atoms.

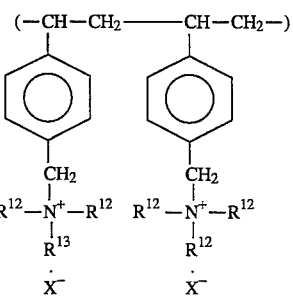

wherein the groups $R^{12}$ are the same or different and are each alkyl having 1 to 4 carbon atoms, $R^{13}$ is alkyl having 14 to 20 carbon atoms, and $X^-$ is an anion.

However, these known antibacterial polymers are not fully satisfactory in antibacterial activity.

The antibacterial polymer is prepared by reacting a tertiary amine with a polymer having a reactive chlorine group in its side chain to substitute the tertiary amine for the reactive chlorine group, whereas difficulty is encountered in completely effecting the substitution, consequently permitting many active chlorine-containing functional groups to remain in the molecule. Accordingly, the antibacterial polymer itself problems in respect of stability and safety to the human body.

To overcome these problems, antibacterial polymers are also prepared by synthesizing an antibacterial polymerizable monomer and copolymerizing the monomer with other monomer. For example, antisoiling coating compositions are known which comprise as an effective component a copolymer containing a monomer represented by the general formula (5) (JP-A-64167/1990).

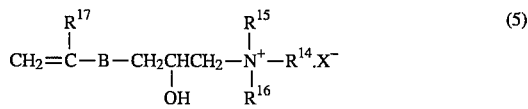

wherein $R^{14}$ is a straight-chain or branched alkyl or alkenyl having 8 to 22 carbon atoms, $R^{15}$ and $R^{16}$ are each alkyl having 1 to 3 carbon atoms, $R^{17}$ is a hydrogen atom or methyl, B is O—CO or O—CH$_2$, and X is a monovalent anion.

Further according to a report of Senuma et al., polymers are prepared by reacting chloromethylstyrene with cetyldimethylamine [$C_{16}H_{33}N(CH_3)_2$] to obtain a quaternary ammonium salt polymer represented by the general formula (6), and copolymerizing the monomer with acrylonitrile [High-Polymer Fiber Material Research Institute, Research Report, No. 159 (1988), pp. 17~22]. However, these polymers still remain to be improved in antibacterial activity.

Further U.S. Pat. No. 4,009,201 discloses that a polymer is produced by preparing a cationic monomer represented, for example, by the formula (7) and polymerizing the monomer, but merely states that the polymer is for use as an absorber or is useful for giving improved antistatic or pigment accepting effects, and says nothing whatever about antibacterial applications. Additionally, the monomer, wherein a polymerizable vinyl group is linked to a functional group having a cationic group by arm ester group, is susceptible to hydrolysis, so that the polymer derived from the cationic monomer has the problem that the side chain containing the cationic group (diammonium group) dissolves out as released from the polymer main chain to impair the function of the polymer.

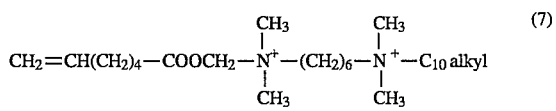

Among these researches, we have already found the compounds disclosed in U.S. Pat. No. 4,826,924 and the compounds disclosed in JP-A-342504/1992 as compounds which are especially excellent in antibacterial activity. These compounds are prepared conventionally by reacting a tertiary amine with a polymer having a reactive chlorine group on the side chain and substituting the tertiary amine for the reactive chlorine group, whereas it is difficult to completely effect the substitution of the tertiary amine or like compound having a great molecular weight. The reaction therefore requires a prolonged period of time or involves the likelihood that the chlorine group will remain unreacted in the molecule to impair the safety and stability of the polymer.

Accordingly, we have conducted continued research to ensure higher safety and, at the same time, to simplify the reaction process. In the course of the research, an attempt was made, for example, to substitute a third component, such as an alkyl ammonium salt, which is lower in molecular weight and easy to substitute, for the unreacted chlorine group, and a corresponding result was achieved. To obtain the desired composition with greater ease, the result was nevertheless still unsatisfactory from the viewpoint of simplifying the reaction process and the stability of the polymer in respect of quaternization and polydispersity.

Further in the case of compounds (2) wherein A is phenylene which may have a substituent, a problem arises when the compound is present in a medium, such as water or alcohol, which has nucleophilic reactivity. Since the benzyl group is highly reactive, the compound is likely to decompose in the solvent, permitting the amine-containing side chain to become released or becoming degraded or insoluble while being stored for a long period. Furthermore, since the compound is not always fully amenable to adsorption to a wide variety of carriers, articles for example of acrylic, urethane or like sheet or fibers having the compound applied thereto fail to semipermanently retain an antibacterial effect. To solve this problem, we have devoted efforts to the preparation and screening of peripheral substances and found substances having high safety for use in such a field.

An object of the present invention is to provide a polymerizable monomer for readily giving an antibacterial polymer which is excellent in bactericidal activity, high in safety and stability and capable of retaining its effect for a prolonged period of time even in a reactive environment, and to provide the polymer and a process for preparing the same.

The present invention provides a polymerizable monomer represented by the general formula (1)

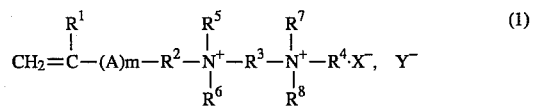

wherein $R^1$ is a hydrogen atom, methyl, chlorine or cyano, $R^2$ is alkylene having 1 to 4 carbon atoms, $R^3$ is alkylene having 3 to 10 carbon atoms, $R^1$ is alkyl having 6 to 18 carbon atoms, $R^5$ to $R^8$ are the same or different and are each alkyl or substituted alkyl having 1 to 3 carbon atoms, A is methylene, phenylene, substituted phenylene, $-CH_2O-$, $-CH_2CH_2O-$, $-CO-$, $-CO-N(R^9)-$ (wherein $R^9$ is a hydrogen atom or methyl) or vinylene, m is 0 or 1, and X and Y are the same or different, and are each a monovalent anion or form a bivalent anion when taken together.

The present invention further provides a polymer which has a structural unit derived from noncrosslinkable or crosslinkable vinyl monomer or from a mixture of such monomers, and a structural unit represented by the general formula (2)

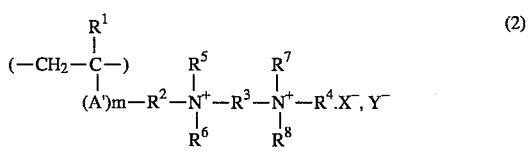

wherein $R^1$ is a hydrogen atom, methyl, chlorine or cyano, $R^2$ is alkylene having 1 to 4 carbon atoms, $R^3$ is alkylene having 3 to 10 carbon atoms, $R^4$ is alkyl having 6 to 18 carbon atoms, $R^5$ to $R^8$ are the same or different and are each alkyl or substituted alkyl having 1 to 3 carbon atoms, A' is methylene, $-CH_2O-$, $-CH_2CH_2O-$, $-CO-$, $-CO-N(R^9)-$ (wherein $R^9$ is a hydrogen atom or methyl) or vinylene, m is 0 or 1, and X and Y are the same or different, and are each a monovalent anion or form a bivalent anion when taken together.

The present invention further provides a process for preparing a polymer characterized by polymerizing a noncrosslinkable or crosslinkable vinyl monomer or a mixture of such monomers with a monomer represented by the general formula (1).

The present invention further provides a disinfectant composition comprising the polymer for destroying bacteria which are resistant to antibiotics.

The present invention further provides a method of imparting antibacterial properties to fibers by applying the polymer to the fibers.

In the compound represented by the general formula (1), especially preferable as the alkylene group represented by $R^3$ is a group having 4 to 6 carbon atoms from the viewpoint of antibacterial properties. Further preferable as the alkyl group represented by $R^4$ is a group having 10 to 14 carbon atoms from the viewpoint of antibacterial properties because it is thought that the hydrophobicity of the functional group and the electron density of quaternary ammonium on the functional group have a close relation with antibacterial properties.

With reference to the general formula (1), examples of substituents on the substituted phenylene represented by A are halogen atom such as fluorine, chlorine, bromine and iodine, lower alkyl such as methyl, ethyl, propyl and butyl, lower alkoxyl such as methoxy, ethoxy, propoxy and butoxy. Although the anions represented by X and Y are not limited specifically insofar as they are capable of neutralizing positive charges, examples of useful anions are monovalent anion such as chlorine ion, bromine ion, iodine ion, nitrate on, perchloration, acetate ion, methylsulfate ion, benzenesulfonate ion, chlorobenzenesulfonate ion and toluene sulfonate ion, bivalent anion such as sulfate ion and methyl phosphate ion.

Among the compounds of the general formula (1), the compound (1a) wherein the group represented by A is methylene, phenylene, substituted phenylene, —CO—, —CO—N($R^9$)— (wherein $R^9$ is as defined above) or vinylene can be prepared, for example, by reacting a compound represented by the general formula (8) with a compound represented by the general formula (9).

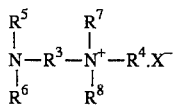 (8)

wherein $R^3$ to $R^8$ and X are as defined above.

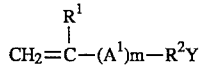 (9)

wherein $R^1$, $R^2$, m and Y are as defined above, $A^1$ is methylene, —CO—, —CO—N($R^9$)—, (wherein $R^9$ is as defined above) or vinylene.

The reaction is conducted usually in a solvent, with heating if required. The solvent is not limited specifically insofar as it does not influence the reaction. Examples of useful solvents are methanol, ethanol, propanol and like alcohols, dimethyl ether, tetrahydrofuran and like ethers, benzene, toluene and like aromatic hydrocarbons, dichloromethane, carbon tetrachloride and like halogensted hydrocarbons, acetone, ethyl acetate, dimethyl sulfoxide and dimethylformamide. Since the desired product (2a) and the compound (9) are both polymerizable, the reaction may be conducted with a usual polymerization inhibitor, such as hydroquinone or catechol, added to the reaction system when so required. The mixing ratio of the compound (9) to the compound (8) is not limited specifically but can be determined suitably from a wide range. The compound is used usually in an amount of about 0.7 to about 0.2 moles, preferably about 0.9 to about 1.0 mole, per mole of the compound (8).

The mono quaternary ammonium salt derivative of the general formula (8) is prepared, for example, by reacting an alkanediamine derivative substituted with lower alkyl and represented by the general formula (10) with a compound represented by the general formula (11) in a solvent or in the absence of solvent, with application of heat when required.

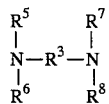 (10)

wherein $R^3$ and $R^5$ to $R^8$ are as defined above.

 (11)

wherein $R^4$ is as defined above.

The solvent is not limited specifically insofar as it produces no influence on the reaction. Examples of useful solvents are methanol, ethanol and like lower alcohols, acetonitrile and like nitriles, and tetrahydrofuran and like ethers. Although the mixing ratio of the compound (10) to the compound (11) is not limited specifically, usually about 1.0 to about 5 moles, preferably about 1.2 to about 4 moles, of the compound (10) is used per mole of the compound (11).

Examples of useful compounds (10) are N,N,N',N'-tetramethyl-1,3-propanediamine, N,N,N',N'-tetramethyl-1,4-butanediamine, N,N,N',N'-tetramethyl-1,5-pentanediamine, N,N,N',N'-tetramethyl-1,6-hexanediamine, N,N,N',N'-tetramethyloctanediamine, N,N,N',N'-tetramethyldecanediamine, N,N,N',N'-tetraethylethylenediamine, N,N,N',N'-tetraethyl-1,3-propanediamine, N,N,N',N'-tetraethyl-1,4-butanediamine, N,N,N',N'-tetraethyl-1,5-pentanediamine and N,N,N',N'-tetraethyl-1,6-hexanediamine. Examples of useful compounds (11) are those having about 6 to about 18 carbon atoms, such as alkyl chloride, alkyl bromide, alkyl iodide, alkyl benzenesulfonate, alkyl chlorobenzenesulfonate and alkyl toluenesulfonate.

Examples of useful compounds (9) are alkyl halides or methallyl halides wherein the halogen atom is chlorine, bromine or iodine, allyl benzenesulfonate, allyl chlorbenzenesulfonate, allyl toluenesulfonate, chloromethylstyrene, chloromethyl vinyl ketone, bromomethyl vinyl ketone, methallyl benzenesulfonate, methallyl chlorobenzenesulfonate, methallyl toluenesulfonate, α-methyl (chloromethyl) styrene, α-chloro (chloromethyl) styrene, α-cyano (chloromethyl) styrene, α-chloromethylacrylonitrile, N-2-chloroethylacrylamide, N-2-bromoethylacrylamide, N-methyl-N-2-bromoethylacrylamide, N-2-bromoethylmethacrylamide, N-methyl-N-2-bromoethylmethacrylamide, N-2-tosyloxyethylacrylamide and N-methyl-N-2-tosyloxyethylmethacrylamide.

The compound (1b) of the formula (1) wherein the group represented by A is —$CH_2O$— or —$CH_2CH_2O$— can be prepared, for example, by reacting a compound represented by the general formula (12) with a compound represented by the general formula (13).

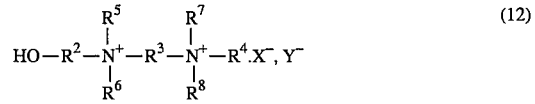 (12)

wherein $R^2$ to $R^8$, X and Y are as defined above.

 (13)

wherein $R^1$ is as defined above, $A^2$ is methylene or ethylene, Z is a halogen atom, lower alkoxyl having 1 to 4 carbon atoms, lower acyloxy having 2 to 5 carbon atoms, benzenesulfonyloxy, chlorobenzenesulfonyloxy, tosyloxy or methanesulfonyloxy. Examples of lower acyloxy groups are acetyloxy, propionyloxy, butyryloxy and valeryloxy.

The reaction is carried out usually in a solvent in the presence of a base, with application of heat when required. The solvent is not limited specifically insofar as it produces no influence on the reaction. Examples of useful solvent are ether, tetrahydrofuran, dichloromethane, chloroform, dimethylformamide, dimethyl sulfoxide, etc. Since the desired product (2b) and the compound (13) are both polymerizable, the reaction may be carried out with hydroquinone, catechol or like usual polymerization inhibitor added to the reaction system when so required. The base is used usually in an approximately stoichiometric amount although the amount is not limited specifically. While the mixing ratio of the compound (12) to the compound (13) is not limited specifically, usually about 0.7 to about 1.2 moles, preferably about 0.9 to about 1.0 mole, of the compound (12) is used per mole of the compound (13).

The base to be used is not limited specifically but can be a usual one. Examples of useful bases include inorganic bases such as sodium hydroxide, potassium hydroxide and sodium carbonate, and organic bases such as pyridine, piperidine, diisopropylamine, triethylamine and diazabicyclooctane.

Examples of useful compounds (13) are allyl halides or methallyl halides wherein the halogen atom is chlorine, bromine or iodine, 4-bromo-1-butene, 3-butenyl toluenesulfonate, esters of benzenesulfonic acid, toluenesulfonic acid or chlorobenzenesulfonic acid with allyl alcohol or methallyl alcohol, and 2,3-dichloropropene.

The compound (12), which is a known substance, can be prepared, for example, by reacting a compound (8) with a compound represented by the general formula (14).

HO—R²Y     (14)

wherein R² and Y are as defined above.

The reaction is conducted usually in a solvent which will not exert any influence on the reaction while heating the reaction system when so required. Although the mixing ratio of the compound (14) to the compound (8) is not limited specifically, usually about 1.0 to about 3 moles, preferably about 7.2 to about 2 moles, of the compound (14) is used per mole of the compound (8). Examples of useful compounds (14) are 2-halogeno-1-ethanol, 3-halogeno-1-propanol, 4-halogeno-1-butanol, 3-halogeno-2-methyl-1-propanol (wherein halogen atom is chlorine, bromine, iodine atom, etc.), 2-hydroxyethyl benzenesulfonate, 2-hydroxyethyl toluenesulfonate, 3-hydroxypropyl toluenesulfonate and 4-hydroxybutyl toluenesulfonate.

The compound (12) can also be produced, for example, by the process comprising protecting the hydroxyl group of the compound (14) with a suitable functional group W to obtain a compound represented by the general formula (14a), reacting this compound with the compound (8) to prepare a compound represented by the general formula (12a) and hydrolyzing the resulting compound. The functional group represented by W is, for example, acetyl, tetrahydropyranyl, methoxymethyl, benzenesulfonyl, toluenesulfonyl or the like.

WO—R²Y     (14a)

wherein R² and Y is as defined above, and W is the functional group.

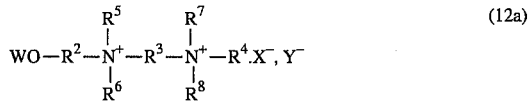

$$WO-R^2-\underset{\underset{R^6}{|}}{\overset{\overset{R^5}{|}}{N^+}}-R^3-\underset{\underset{R^8}{|}}{\overset{\overset{R^7}{|}}{N^+}}-R^4.X^-, Y^-$$     (12a)

wherein R² to R⁸, X, Y and W are as defined above.

The reaction between the compound (8) and the compound (14a) is carried out in a suitable solvent, with application of heat when so required. The solvent is not limited particularly insofar as it exerts no influence on the reaction. For example, the same solvent as is used for preparing the compound (8) is usable. The amount of the compound (14a) to be used is not limited specifically but can be determined suitably from a wide range. It is usually about 1.0 to about 3 moles, preferably about 1.2 to about 2 moles, per mole of the compound (8). Examples of compounds (14a) are 2-halogenoethyl acetate, 2-halogenoethyl tetrahydropyranyl ether, 4-halogenobutyl toluenesulfonate (wherein halogen atom is chlorine, bromine, iodine atom, etc.), ethylene glycol blsbenzenesulfonate and ethylene glycol bistoluenesulfonate.

The compound (12a) is hydrolyzed by a usual method. The compound (12a) can be readily converted to the compound (12), for example, by treating the compound in dilute hydrochloric acid, with heating when necessary.

The compounds (1) and intermediates thereof obtained by the foregoing reactions can be isolated and purified by usual methods such as filtration, extraction, concentration and recrystallization.

The copolymer of the present invention can be produced by subjecting a noncrosslinkable or crosslinkable vinyl monomer or a mixture of such monomers, and the compound (1) to a usual polymerization process such as solution polymerization, solid-phase polymerization, bulk polymerization, emulsion polymerization or suspension polymerization. Among these processes, it is desirable to use the solution polymerization process. The type of solvent to be used for the process is not limited particularly insofar as the solvent produces no adverse effect on the reaction. Examples of solvents usable are protonic solvent such as water, methanol, ethanol and propanol, ether solvent such as ether, tetrahydrofuran and dioxane, halogenated hydrocarbon such as chloroform and carbon tetrachloride, aromatic hydrocarbon such as benzene and toluene, nitrile solvent such as acetonitrile and propionitrile, aprotic polar solvent such as dimethylformamide, dimethyl acetamide, hexamethylphosphoric triamide and dimethyl sulfoxide.

Examples of useful noncrosslinkable vinyl monomers are styrene, p-methylstyrene, p-bromostyrene, p-chlorostyrene, α-chlorostyrene, α-bromostyrene or like polymerizable aromatic compound; acrylic acid, methyl acrylate, ethyl acrylate, lauryl acrylate, methyl α-chloroacrylate, 2-hydroxyethyl acrylate, methyl methacrylate, ethyl methacrylate, propyl methacrylate, butyl methacrylate, lauryl methacrylate or like polymerizable carboxylic acid ester and salt thereof; vinyl acetate, vinyl trifluoroacetate, vinyl butyrate, vinyl benzoate or like vinyl ester monomer; vinyl chloride, vinyl fluoride, vinylidene chloride, vinylidene fluoride or like halogenated vinyl monomer; isobutyl vinyl ether, n-butyl vinyl ether or like vinyl ether monomer; acrylamide, N-methyl acrylamide, N-ethyl acrylamide, N-methyl methacrylamide, N-ethyl methacrylamide or like polymerizable amide; acrylonitrile, methacrylonitrile, α-chloroacrylonitrile, vinylidene cyanide or like polymerizable nitrile; ehtylene, propylene, isobutylene, pentene, hexene, cyclohexene, norbornene, allene, butadiene, isoprene, chloroprene or like olefinic monomer; alkyl vinyl sulfide or like vinyl sulfide monomer; N-vinylcarbazole, 4-vinylpyridine, N-vinylpyrrolidone or like nitrogen-containing heterocyclic monomer; methyl vinyl ketone, phenyl vinyl ketone or like vinyl ketone monomer; maleic acid, maleic anhydride, acrolein, acrylic acid chloride, vinyl isocyanate, vinyl silane, allyl silane, polymerizable monomer represented by the formula (1).

Examples of useful crosslinkable vinyl monomers are divinylbenzene, divinylnaphthalene and the like. These monomers are usable singly, or at least two of them can be used in mixture.

The charge molar ratio of the compound of the formula (1) of the invention to the monomer to be copolymerized therewith is usually about 0.001~99.0: 99.999~1.0, preferably about 1~50 : 99~50.

The polymerization reaction can be conducted efficiently usually in the presence of a polymerization initiator. Examples of useful polymerization initiators are azo initiator such as 2,2'-azobisisobutyronitrile, 2,2'-azobis-2-methylbutyronitrile, 2,2'-azobis-2,4-dimethylvaleronitrile, 1,1'-azobis-1-cyclohexanecarbonitrile and dimethyl-2,2'-azobisisobutyrate, peroxide such as hydrogen peroxide, benzoyl peroxide, t-butyl hydroperoxide, cumene hydroperoxide, ammonium persulfate and potassium persulfate, redox initiator such as a combination of hydrogen peroxide or ammonium persulfate and sodium sulfite or ferrous ion, organic metal compound such as phenylmagnesium bromide and butyl lithium. The amount of the initiator to be used, which differs with the kind thereof, mode of polymerization and desired molecular weight of the copolymer, is usually $1 \times 10^{-5}$–0.5 mole/l, preferably $1 \times 10^{-4}$–$5 \times 10^{-2}$ mole/l.

In the case where the solution polymerization process is employed, the solvent to be used is not limited specifically insofar as it exerts no adverse influence on the reaction. Examples of useful solvents are protonic solvent such as water, methanol, ethanol, propanol, methyl cellosolve and ethyl cellosolve, ether solvent such as ether, tetrahydroluran, dioxane, dimethoxyethane and diglyme, halogenated hydrocarbon such as dichloromethane, chloroform and carbon tetrachloride, aromatic hydrocarbon such as benzene, toluene and xylene, nitrile solvent such as acetonitrile and propionitrile, aprotic polar solvent such as dimethylformamide, dimethyl acetamide, hexamethylphosphoric triamide and dimethyl sulfoxide. At least two of these solvents are usable in mixture.

The reaction temperature and the reaction time, although varying with the reactivity of the monomer and the type of solvent used, are determined preferably from the respective ranges usually of 0° to 100° C. and 3 to 120 hours.

The copolymer can be isolated and purified by a usual method of after treatment. For example, the reaction mixture is added to an excessive amount of solvent in which the product is sparingly soluble to separate out the product, which is then separated off as by filtration. When the product needs to be further purified, reprecipitation or like conventional method is resorted to.

It is desired that the copolymer of the present invention be 1,000 to 2,000,000, preferably 5,000 to 300,000, in number average molecular weight Mn and 1.1 to 2.0 in Mw/Mn (Mw: weight average molecular weight). Since the polymerization degree is governed by factors such as the concentration of charges for the polymeriazation reaction, kind and concentration of the initiator, reaction temperature and reaction time, a copolymer having the desired molecular weight and polydispersity can be obtained by determining these factors in accordance with the situation concerned.

The copolymer obtained is subjected to ion exchange by a known procedure to make the counter anion a monovalent anion such as chlorine ion, bromine ion, iodine ion, nitrate ion, perchlorate ion, acetate ion or methylsulfate ion, or bivalent ion such as sulfate ion or methyl phosphate ion.

For use as the active component, the polymers of the present invention are usable singly, or at least two of them can be used in mixture.

The polymers of the invention can be in the form of a powder, granules, fibers, film or the like depending on the process for preparing the polymer.

In the case where the polymers of the invention are used, for example, as the active component of antibacterial compositions, these compositions are usable for a wide variety of applications, for example, for tap water, cooling water, slime control, pools, fishing nets, ship bottoms, underwater structures, food packaging materials, building materials, agricultural materials, medical products, materials or utensils for use in the oral cavity (toothbrushes, toothpastes etc.), spectacle frames, cosmetics, clothes and household utensils.

The present antibacterial polymers are usable by known methods. For example, for the antibacterial surface treatment of articles, the article can be treated by being dipped in or sprayed with a solution prepared by dissolving one or at least two of the polymers in a suitable solvent. At this time, the polymer is usable as admixed with known polymers.

The materials for which the antibacterial polymers are usable are, for example, synthetic high polymers of any form such as polypropylene, polyethylene, polystyrene, polyester, polyamide, polyacrylate, polyurethane and polyvinyl chloride, natural high polymers such as cotton, wool, feathers, hemp, silk, paper and rubber, and further wood, glass, metal and ceramics.

These materials may be in the form of molded or shaped materials, or unprocessed materials. The material to be subjected to the antibacterial treatment can be in the form of yarns, fibers, film, sheet, grains, powder or the like.

The polymers of the present invention impart high antibacterial activity to these materials with high safety over a prolonged period of time.

When the antibacterial polymers are to be used, it is generally preferable to use the polymer as dissolved in methyl alcohol, ethyl alcohol, n-propyl alcohol, isopropyl alcohol, n-butyl alcohol, isobutyl alcohol, N,N-dimethylformamide, N,N-dimethylacetamide, dimethyl sulioxide or the like, or in a solvent mixture of such a solvent and acetone, tetrahydrofuran, benzene, toluene, xylene or the like. The concentration of the solution is 0.01 to 2.0 wt. %, preferably 0.1 to 1.0 wt. %. The substance to be given antibacterial properties is dipped in or sprayed with the solution, whereby the solution is applied to the surface, followed by drying to remove the solvent. It is desirable to dry the wet substance in a drying chamber at a temperature of 0° to 80° C., preferably 20° to 60° C. for 10 to 48 hours.

The antibacterial polymers are also excellent in underwater antisoiling properties. When to be used underwater for preventing soiling, the antibacterial polymer is usable as admixed with a known coating composition. Known substances containing an antisoiling component can be added to the mixture.

For underwater antisoiling applications, the antibacterial polymers are usable, for example, for fishing nets, ship bottoms, cooling water piping, buoys, dam gates, water tanks of culture facilities and underwater structures, and are very effective for preventing adhesion of sea weed, green layer, sea lettuce, barnacles, etc.

When the antibacterial polymers are to be used for underwater antisoiling applications, it is generally desirable to dissolve the polymer in a solvent such as methyl alcohol, ethyl alcohol, n-propyl alcohol, isopropyl alcohol, n-butyl alcohol, N,N-dimethylformamide or dimethyl sulfoxide, or in a solvent mixture of such a solvent and benzene, toluene, xylene or the like. The method of use can be a known method.

The known substance containing an antisoiling component and usable as admixed with the antibacterial polymer is not limited particularly. Examples of such substances are copper compounds, dithiocarbamate compounds, phenarsazine compounds, quaternary ammonium salt compounds, etc. Also usable as admixed with the antibacterial polymer are crosslinking agents, fillers, monomers, polymers and the like which have antisoiling activity.

Next, the coating composition usable as mixed with the antibacterial polymer may be any of those already known, which include, for example, acrylic acid resin, phthalic acid resin, aminoalkyd resin and synthetic resin emulsion compositions, lacquers, etc.

BEST MODE OF CARRYING OUT THE INVENTION

The invention will be described in detail with reference to the following examples.

EXAMPLE 1

A 23.1 g quantity (0.16 mole) of N,N,N',N'-tetramethyl-1,4-diaminobutane (hereinafter referred to as "TMB") was dissolved in 50 ml of acetonitrile, and 10.0 g (0.04 mole) of lauryl bromine was added dropwise to the solution at room temperature with stirring, followed by heating at 70° C. for 3 hours. The reaction mixture was then cooled to room temperature, giving a white precipitate, which gave 0.12 g of N,N,N',N'-tetramethyl-1,4-diaminobutane-N,N' -dilauryl dibromide as a by-product (yield of by-product 1.0%) on filtration. The flitrate was concentrated at a reduced pressure to remove a major portion of the TMB and give a white pasty residue. The residue was washed with 40 ml of hexane, and the hexane layer was separated off by decantation, giving a white waxy substance free from any unreacted TMB. When thoroughly dried at a reduced pressure using a vacuum pump, the product gave 14.5 g of N,N,N',N'-tetramethyl-1, 4-N-lauryl bromide (hereinafter abbreviated as "TML-$C_4$", yield 92%). $^1$H-NMR (CDCl$_3$) δppm: 0.83 (t, 3H, CH$_3$), 1.19~1.29 (m, 20H, CH$_2$), 1.60–2.00 (m, 6H, CH$_2$), 2.68 (s, 6H, CH$_3$—N), 3.05 (s, 6H, CH$_3$—N), 3.15~3.28 (m, 2H, CH$_2$N), 3.37~3.45 (m, 2H, CH$_2$N)

EXAMPLES 2 TO 5

The same reaction and aftertreatment as in Example 1 were repeated except that TMB was replaced by 20.8 g (0.16 mole) of N,N,N',N'-tetramethyl-1,3-diaminopropane (hereinafter abbreviated as "TMP"), 27.5 g (0.16 mole) of N,N,N',N' -tetramethyl- 1,6-diaminohexane (hereinafter abbreviated as "TMH"), 36.5 g (0.16 mole) of N,N,N',N'-tetramethyl-1,10-diaminodecane (hereinafter abbreviated as "TMD") or 36.5 g (0.16 mole) of N,N,N',N'-tetraethyl -1,6-diaminohexane (hereinafter abbreviated as "TEH"), whereby the desired mono-quaternary ammonium salt derivatives were obtained. The reaction yielded a small amount of bis-quaternary ammonium salt derivative as a by-product. Table 1 shows the result, in which Et stands for ethyl.

EXAMPLES 6 AND 7

The desired mono-quaternary ammonium salt derivatives were obtained by repeating the same reaction and aftertreatment as in Example 1 with the exception of using 27.5 g (0.16 mole) of TMH in place of TMB and 8.8 g (0.04 mole) of decyl bromide or 13.3 g (0.04 mole) of octadecyl bromide instead of lauryl bromide. The reaction yielded a small of bis-quaternary ammonium salt derivative as a by-product. Table 1 also shows the result.

TABLE 1

| Ex. | Compound (10) | Compound (11) | Compound (8) | Yield (%) |
|---|---|---|---|---|
| 2 | \|N—(CH$_2$)$_3$—N\| | C$_{12}$H$_{25}$Br | \|N—(CH$_2$)$_3$—N$^+$\|—C$_{12}$H$_{25}$·Br$^-$ (TML-C$_3$) | 94 |
| 3 | \|N—(CH$_2$)$_6$—N\| | C$_{12}$H$_{25}$Br | \|N—(CH$_2$)$_6$—N$^+$\|—C$_{12}$H$_{25}$·Br$^-$ (TML-C$_6$) | 90 |
| 4 | \|N—(CH$_2$)$_{10}$—N\| | C$_{12}$H$_{25}$Br | \|N—(CH$_2$)$_{10}$—N$^+$\|—C$_{12}$H$_{25}$·Br$^-$ (TML-C$_{10}$) | 84 |
| 5 | Et\|N—(CH$_2$)$_6$—N\|Et / Et Et | C$_{12}$H$_{25}$Br | Et\|N—(CH$_2$)$_6$—N$^+$\|—C$_{12}$H$_{25}$·Br$^-$ / Et Et (TEL-C$_6$) | 91 |
| 6 | \|N—(CH$_2$)$_6$—N\| | C$_{10}$H$_{21}$Br | \|N—(CH$_2$)$_6$—N$^+$\|—C$_{10}$H$_{21}$·Br$^-$ (TMD-C$_6$) | 92 |
| 7 | \|N—(CH$_2$)$_6$—N\| | C$_{18}$H$_{37}$Br | \|N—(CH$_2$)$_6$—N$^+$\|—C$_{18}$H$_{37}$·Br$^-$ (TMO-C$_6$) | 83 |

EXAMPLE 8

A 11.1 g quantity (26.4 mmoles) of TML-C$_6$ obtained in Example 3 was dissolved in 200 ml of acetone, and 3.7 g (24 mmoles) of 4-chloromethylstyrene was added dropwise to the solution at room temperature with stirring. When the mixture was then heated at 50° C. for 17 hours, white crystals separated out. The reaction mixture was cooled to room temperature, and the resulting white crystals were isolated by filtration, washed with cold acetone and thereafter dried, affording 12.0 g of N,N,N',N'-tetramethyl-N- lauryl-N'-(4-vinyl) benzylhexamethylene diammonium bromide chloride (hereinafter abbreviated as "TMLS-C$_6$", yield 87%). $^1$H-NMR (CDCl$_3$)δppm: 0.86 (t, 3H, CH$_3$), 1.92~1.37 (m, 18H, CH$_2$), 1.53~1.73 (m, 6H, CH$_2$), 1.98~2.21 (m, 4H, CH$_2$), 3.26 (s, 6H, CH$_3$N), 3.37 (s, 6H, CH$_3$N), 3.40~3.50 (m, 2H, CH$_2$N), 3.68~3.87 (m, 4H, CH$_2$N), 4.95 (s, 2H, CH$_2$ Ar), 5.38 (d, 1H, vinyl), 5.81 (d, 1H, vinyl), 6.7 (dd, 1H, vinyl), 7.46 (d, 2H, ArH), 7.62 (d, 2H, ArH)

EXAMPLES 9 TO 12

The desired bis-quaternary ammonium salt derivatives were obtained by repeating the same reaction and aftertreatment as in Example 8 with the exception of using 2.90 g (24 mmoles) of allyl bromide, 3.24 g (24 mmoles) of 4-bromo-1-butene, 3.58 g (24 mmoles) of bromomethyl vinyl ketone or 6.79 g (24 mmoles) of N-2-tosyloxyethylacrylamide in place of 4-chloromethylstyrene and using acetone or ethyl acetate as a solvent. Table 2 shows the result.

12.4 g (26 mmoles) of TEL-C$_6$. in place of TML-C$_6$. Table 3 shows the result.

TABLE 2

| Ex. | Compound (8) (solvent) | Compound (9) | Compound (1) | Yield (%) |
|---|---|---|---|---|
| 9 | TML-C$_6$ (ethyl acetate) | allyl bromide (CH$_2$=CHCH$_2$Br) | CH$_2$=CH-CH$_2$-N$^+$-(CH$_2$)$_6$-N$^+$-C$_{12}$H$_{25}$·2Br$^-$ (TMLA-C$_6$) | 94 |
| 10 | TML-C$_6$ (ethyl acetate) | 4-bromo-1-butene | CH$_2$=CH-(CH$_2$)$_2$-N$^+$-(CH$_2$)$_6$-N$^+$-C$_{12}$H$_{25}$·2Br$^-$ (TMLB-C$_6$) | 88 |
| 11 | TML-C$_6$ (ethyl acetate) | CH$_2$=CH-COCH$_2$Br | CH$_2$=CH-CH$_2$-N$^+$-(CH$_2$)$_6$-N$^+$-C$_{12}$H$_{25}$·2Br$^-$ (TMLK-C$_6$) | 86 |
| 12 | TML-C$_6$ (ethyl acetate) | CH$_2$=C(CH$_3$)-CONH(CH$_2$)$_2$OTs | CH$_2$=C(CH$_3$)-CONH(CH$_2$)$_2$N$^+$(CH$_2$)$_6$N$^+$C$_{12}$H$_{25}$ (TMLC-C$_6$) ·Br$^-$·OTs$^-$ | 80 |

EXAMPLES 13 TO 18

The desired bis-quaternary ammonium salt derivatives were obtained by repeating substantially the same reaction and aftertreatment as in Example 8 with the exception of using 9.09 g (24 mmoles) of TML-C$_3$, 9.43 g (24 mmoles) of TML-C$_4$, 12.4 g (26 mmoles) of TML-C$_{10}$, 10.2 g (26 mmoles) of TMD-C$_6$, 13.1 g (26 mmoles) of TMO-C$_6$ or

TABLE 3

| Ex. | Compound (8) (solvent) | Compound (9) | Compound (1) | Yield (%) |
|---|---|---|---|---|
| 13 | TML-C$_3$ (acetone) | CH$_2$=CH-C$_6$H$_4$-CH$_2$Cl | CH$_2$=CH-C$_6$H$_4$-CH$_2$-N$^+$-(CH$_2$)$_3$-N$^+$-C$_{12}$H$_{25}$ (TMLV-C$_3$) ·Cl$^-$·Br$^-$ | 95 |

TABLE 3-continued

| Ex. | Compound (8) (solvent) | Compound (9) | Compound (1) | Yield (%) |
|---|---|---|---|---|
| 14 | TML-C$_4$ (acetone) | CH$_2$=CH-C$_6$H$_4$-CH$_2$Cl | CH$_2$=CH-C$_6$H$_4$-CH$_2$-N$^+$(CH$_3$)$_2$-(CH$_2$)$_4$-N$^+$(CH$_3$)$_2$-C$_{12}$H$_{25}$ · Cl$^-$·Br$^-$ (TMLV-C$_4$) | 95 |
| 15 | TML-C$_{10}$ (acetone) | CH$_2$=CH-C$_6$H$_4$-CH$_2$Cl | CH$_2$=CH-C$_6$H$_4$-CH$_2$-N$^+$(CH$_3$)$_2$-(CH$_2$)$_{10}$-N$^+$(CH$_3$)$_2$-C$_{12}$H$_{25}$ · Cl$^-$·Br$^-$ (TMLV-C$_{10}$) | 90 |
| 16 | TMD-C$_6$ (acetone) | CH$_2$=CH-C$_6$H$_4$-CH$_2$Cl | CH$_2$=CH-C$_6$H$_4$-CH$_2$-N$^+$(CH$_3$)$_2$-(CH$_2$)$_6$-N$^+$(CH$_3$)$_2$-C$_{10}$H$_{21}$ · Cl$^-$·Br$^-$ (TMDV-C$_6$) | 82 |
| 17 | TMO-C$_6$ (acetone) | CH$_2$=CH-C$_6$H$_4$-CH$_2$Cl | CH$_2$=CH-C$_6$H$_4$-CH$_2$-N$^+$(CH$_3$)$_2$-(CH$_2$)$_6$-N$^+$(CH$_3$)$_2$-C$_{18}$H$_{37}$ · Cl$^-$·Br$^-$ (TMOV-C$_6$) | 87 |
| 18 | TEL-C$_6$ (acetone) | CH$_2$=CH-C$_6$H$_4$-CH$_2$Cl | CH$_2$=CH-C$_6$H$_4$-CH$_2$-N$^+$(Et)$_2$-(CH$_2$)$_6$-N$^+$(Et)$_2$-C$_{12}$H$_{25}$ · Cl$^-$·Br$^-$ (TELV-C$_6$) | 89 |

EXAMPLE 19

A 8.42 g quantity (20 mmoles) of TML-C$_6$ obtained in Example 3 was dissolved in 200 ml of methanol, and 2.78 g (20 mmoles) of 3-bromo-1-propanol was added to the solution of room temperature. The mixture was then reacted at 50° C. with heating for 12 hours and thereafter concentrated at a reduced pressure to obtain 11.1 g of white solid reaction. The residue was placed into 100 ml of ethyl acetate, followed by washing and then by filtration to remove the resulting solution layer. When dried, the cake gave 9.96 g of N,N,N',N'-tetramethyl-N-(3-hydroxy) propyl-N'-lauryl-hexamethylene diammonium dibromide (TMLP-C$_6$) in the form of white crystals (yield 89%). $^1$H-NMR (CDCl$_3$) δppm: 0.87 (t, 3H, CH$_3$), 1.20~1.57 (m, 26H, CH$_2$), 1.63~1.80 (m, 4H, CH$_2$), 3.25 (t, 2H, CH$_2$ O), 3.39 (s, 6H, CH$_3$N), 3.50 (s, 6H, CH$_3$N), 3.45~3.59 (m, 8H, CH$_2$ N)

EXAMPLE 20

Substantially the same reaction and aftertreatment as in Example 19 were repeated except that 3-bromo-1-propanol was replaced by 4.88 g (20 mmoles) of 4-tosyloxy-1-butanol, whereby 10.2 g of N,N,N',N'-tetramethyl-N-(4-hydroxy)butyl-N'-laurylhexamethylene diammonium bromide toluenesulfonate (TMLB-C$_6$) was obtained in the form of white crystals (yield 91%). $^1$H-NMR (CDCl$_3$) δppm: 0.87 (t, 3H, CH$_3$) , 1.20~1.56 (m, 30H, CH$_2$), 1.63~1.82 (m, 4H, CH$_2$), 2.25 (s , 3H, CH$_3$Ar), 3.39 (s, 6H, CH$_3$N), 3.49 (s, 6H, CH$_3$N), 3.35~3.63 (m, 8H, CH$_2$N), 7.55 (d, 2H, ArH) , 7.86 (d, 2H, ArH)

EXAMPLE 21

A 16.8 g quantity (40 mmoles) of TML-C$_6$ obtained in Example 3 was dissolved in 200 ml of acetone, and 6.67 g (40 mmoles) of 2-bromoethyl acetate was added to the solution at room temperature. The mixture was then reacted at 50° C. for 12 hours to obtain white crystals, which was then isolated by filtration, affording 23.1 g of N,N,N',N'-tetramethyl-N-(2 -acetoxy)ethyl-N'-laurylhexamethylene diammonium dibromide. The product was dissolved in 120 ml of 2% dilute hydrobromic acid, followed by stirring at 60° C. for 15 hours. The resulting reaction mixture was concentrated at a reduced pressure to obtain a light yellow waxy residue, which was then placed into ethyl acetate, followed by washing and then by filtration for the removal of a solution layer. The cake was dried, affording 17.9 g of N,N,N',N'-tetramethyl-N-(2 -hydroxy)ethyl-N'-laurylhexamethylene diammonium dibromide (TMLE-C$_6$) in the form of substantially white crystals (yield 82%). $^1$H-NMR (CDCl$_3$) δppm: 0.86 (t, 3H, C$_3$), 1.22~1.56 (m, 24H, CH$_2$), 1.63~1.79 (m, 4H, CH$_2$), 3.26 (t, 2H, CH$_2$O ), 3.40 (s, 6H, CH$_3$N), 3.51 (s, 6H, CH$_3$N), 3.46~3.60 (m, 8H, CH$_2$N)

EXAMPLE 22

A 5.46 g quantity (10 mmoles) of TMLE-C$_6$ obtained in Example 21 and 1.45 g (12 mmoles) of allyl bromide were dissolved in 50 ml of dichloromethane, and 1.01 g (10 mmoles) of triethylamine was added dropwise to the solution at room temperature with stirring. The mixture was stirred at 40° C. for 15 hours and then cooled to room temperature to form a white precipitate, which was filtered off. Concentration of the filtrate afforded a light yellow waxy residue. The residue was thoroughly washed with acetone and thereafter dried, giving 4.2 g of N,N,N',N'-tetramethyl-N-(2-allyloxy) ethyl-N'-laurylhexamethylene diammonium dibromide (TML2A-C$_6$) in the form of substantially white crystals (yield 72%). $^1$H-NMR (CDCl$_3$) δppm: 0.86 (t, 3H, CH$_3$), 1.22~1.57 (m, 24H, CH$_2$ ), 1.63~1.80 (m, 4H, CH$_2$), 3.12 (d, 2H, CH$_2$ O), 3.26 (t, 2H, CH$_2$ O), 3.40 (s, 6H, CH$_3$N), 3.52 (s, 6H, CH$_3$N), 3.45~3.60 (m, 8H, CH$_2$N), 5.39 (d, 1H, vinyl), 5.68 (m, 1H, vinyl), 5.92 (d, 1H, vinyl)

EXAMPLE 23

A 3.44 g quantity (6 mmoles) of TMLS-C$_6$ and 5.62 g (54 mmoles) of styrene were dissolved in 10 ml of methanol, and a solution of 50 mg (0.3 mmole) of AIBN in 2 ml of methanol was added to the solution. When the mixture was stirred in a nitrogen atmosphere at 65° C. for 22 hours, the mixture became a consistent solution. The reaction mixture was placed into water to terminate the polymerization reaction, and a white polymer formed was isolated by filtration and dried at a reduced pressure. The white polymer obtained was dissolved again in methanol, and the solution was placed into water. This procedure was repeated twice for purification and drying, whereby 6.3 g of white powdery polymer was obtained. The white powdery product was found to be a copolymer of TMLS-C$_6$ and styrene by TLC, IR and $^1$H-NMR analyses. When analyzed by GPC (based on polystyrene) using dimethylformamide as a solvent, the copolymer was 158,000 in Mn and 1.4 in polydispersity Mw/Mn. Quantitative determination of the quaternary ammonium content by colloidal titration with use of polyvinyl sulfate potassium indicated that the TMLS-C$_6$/styrene ratio of the copolymer was 73:87.

EXAMPLE 24

A white powdery polymer (5.9 g) was obtained by repeating the same reaction and aftertreatment as in Example 23 except that TMLS-C$_6$ was replaced by 3.79 g (6 mmoles) of TMLV-C$_3$. When analyzed by TLC, IR and $^1$H-NMR, the white polymer was found to be a copolymer of TMLV-C$_3$ and styrene.

Similarly, when analyzed by GPC, the copolymer was found to be 86,000 in Mn and 7.8 in polydispersity Mw/Mn. Quantitative determination of the quaternary ammonium content by colloidal titration indicated that the TMLV-C$_3$/styrene ratio of the copolymer was 9:91.

EXAMPLES 25 AND 26

White powdery polymers (6.3 g and 6.4 g) were prepared by repeating the same reaction and aftertreatment as in Example 23 except that TMLS-C$_6$ was replaced by 3.26 g (6 mmoles) of TMLV-C$_4$ or 3.78 g (6 mmoles) of TMLV-C$_{10}$. When analyzed by TLC, IR and $^1$H-NMR, these polymers were found to be copolymers of TMLV-C$_4$ or TMLV-C$_{10}$, and styrene.

GPC and colloidal titration conducted in the same manner as in Example 23 revealed that the copolymer comprising TMLV-C$_4$ was 172,000 in Mn, 2.0 in polydispersity Mw/Mn and 16:84 in the TMLV-C$_4$/styrene ratio, and that the copolymer comprising TMLV-C$_{10}$ was 62,000 in Mn, 2.2 in polydispersity Mw/Mn and 7:93 in TMLV-C$_{10}$/styrene ratio.

EXAMPLES 27 AND 28

White powdery polymers (6.6 g and 6.4 g) were prepared by repeating the same reaction and aftertreatment as in Example 23 except that TMLS-C$_6$ was replaced by 3.27 g (6 mmoles) of TMDV-C$_6$ or 3.95 g (6 mmoles) of TMOV-C$_6$. When analyzed by TLC, IR and $^1$H-NMR, these polymers were copolymers comprising TMDV-C$_6$ or TMOV-C$_6$.

GPC and colloidal titration conducted in the same manner as in Example 23 revealed that the copolymer comprising TMDV-C$_6$ was 124,000 in Mn, 2.0 in polydispersity Mw/Mn and 18:82 in the TMDV-C$_6$/styrene ratio, arid that the copolymer comprising TMOV-C$_6$ was 81,000 in Mn, 1.9 in polydispersity Mw/Mn and 9:91 in the TMOV-C$_6$/styrene ratio.

EXAMPLE 29

TMLS-C$_6$ (6.88 g, 12 mmoles) and 11.2 g (108 mmoles) of styrene were dissolved in 12 ml of methanol, and a solution of 32 mg (0.19 mmole) of AIBN in 1 ml of methanol was added to the solution. The mixture became a consistent solution when stirred in a nitrogen atmosphere at 65° C. for 39 hours. The solution was aftertreated in substantially the same manner as in Example 23 to obtain 13.7 g of a white powdery polymer. The white polymer was found to be a copolymer of TMLS-C$_6$ and styrene by TLC, IR and $^1$H-NMR analyses.

When similarly analyzed by GPC, the copolymer was found to be 480,000 in Mn and 1.9 in polydispersity Mw/Mn. Quantitative determination of the quaternary ammonium content by colloidal titration revealed that the TMLS-C$_6$/styrene ratio was 10:90.

EXAMPLE 30

TMLS-C$_6$ (6.88 g, 12 mmoles) and 1.25 g (12 mmoles) of styrene were dissolved in 4 ml of methanol, and a solution of 20 mg (0.12 mmole) of AIBN in 1 ml of methanol was added to the solution. Substantially the same reaction and aftertreatment as in Example 23 were conducted to obtain 6.5 g of a white polymer. The white polymer was found to be a copolymer of TMLS-C$_6$ and styrene by TLC, IR and $^1$H-NMR analyses.

When analyzed by GPC, the copolymer was found to be 200,000 in Mn and 1.6 in polydispersity Mw/Mn. Quantitative determination of the quaternary ammonium content by colloidal titration indicated that the TMLS-C$_6$/styrene ratio was 64:36.

EXAMPLE 31

A white polymer (6.1 g) was obtained by conducting substantially the same reaction and aftertreatment as in Example 23 except that styrene was replaced by 5.40 g (54 mmoles) of methyl methacrylate. TLC, IR and $^1$H-NMR analyses indicated that the polymer was a copolymer of TMLS-C$_6$ and methyl methacrylate in the ratio of about 16:84.

When analyzed by GPC in the same manner as in Example 23, the copolymer was 104,000 in Mn and 1.4 in polydispersity Mw/Mn.

EXAMPLE 32

The same reaction as in Example 23 was effected with the exception of using 3.89 g (54 mmoles) of acrylic acid instead of styrene. The reaction mixture was placed into ether to terminate the polymerization reaction to obtain a white precipitate, which was isolated by filtration and dried to obtain 5.8 g of a white powdery polymer. TLC, IR and $^1$H-NMR analyses revealed that the polymer was a copolymer of TMLS-C$_6$ and acrylic acid in the ratio of about 7:93.

When analyzed by GPC in the same manner as in Example 23, the copolymer was 86,000 in Mn and 1.9 in polydispersity Mw/Mn.

EXAMPLE 33

TMLS-$C_6$ (3.44 g, 6 mmoles) and 8.52 g (60 mmoles) 50% aqueous solution of acrylamide were dissolved in 10 ml of water, and a solution of 50 mg 2,2'-azobis(2-amidopropane) dihydrochloride in 2 ml of water was added to the solution to prepare a uniform solution. The solution was reacted in a nitrogen atmosphere at 50° C. for 2 hours to give a gel of reaction mixture. The gel was placed into an excess of dioxane to terminate the polymerization reaction and form a white polymer, which was then isolated by filtration and dried at a reduced pressure, giving 7.0 g of white polymer. TLC, IR and $^1$H-NMR analyses indicated that the polymer was a copolymer of TMLS-$C_6$ and acrylamide.

GPC analysis and colloidal titration conducted in the same manner as in Example 23 revealed that the copolymer was 328,000 in Mn, 1.9 in polydispersity Mw/Mn and 8:92 in TMLS-$C_6$/acrylamide ratio.

EXAMPLE 34

TMLS-$C_6$ (2.87 g, 5 mmoles) and 4.30 g (50 mmoles) of vinyl acetate were dissolved in 7 ml of dry DMF, and a solution of 41 mg (0.25 mmole) of AIBN in 1 ml of DMF was added to the solution. The mixture became a consistent solution when stirred in a nitrogen atmosphere at 60° C. for 20 hours. The reaction mixture was placed into ether to terminate the polymerization reaction to form a white polymer, which was then isolated by filtration and dried at a reduced pressure, giving 4.6 g of white powder. The powder was found to be a copolymer of TMLS-$C_6$ and vinyl acetate by TLC, IR and $^1$H-NMR analyses. When analyzed by GPC in the same manner as in Example 23, the copolymer was found to be 73,000 in Mn and 1.6 in polydispersity Mw/Mn. Quantitative determination of the quaternary ammonium content by colloidal titration indicated that the copolymer was 19:81 in TMLS-$C_6$/vinyl acetate ratio.

EXAMPLE 35

A white powdery polymer (3.2 g) was obtained by conducting the same reaction and aftertreatment as in Example 34 except that vinyl acetate was replaced by 2.65 g (50 mmoles) of acrylonitrile. TLC, IR and $^1$H-NMR analyses revealed that the polymer was a copolymer of TMLS-$C_6$ and acrylonitrile. The copolymer was found to be 51,000 in Mn and 2.2 in polydispersity Mw/Mn. Quantitative determination oi the quaternary ammonium content by colloidal titration indicated that the copolymer was 17:83 in TMLS-$C_6$/acrylonitrile ratio.

EXAMPLE 36

TMLS-$C_6$ (2.87 g, 5 mmoles), 5.21 g (50 mmoles) of styrene and 0.65 g (5 mmoles) of divinylbenzene were dissolved in 20 ml of methanol, and a solution of 50mg (0.3 mmole) of AIBN in 2 ml of methanol was added to the solution. The mixture gelled when stirred in a nitrogen atmosphere at 60° C. for 19 hours. The reaction mixture was placed into water to obtain a white rubberlike polymer, which was then isolated by filtration and dried at a reduced pressure. The resulting white polymer was washed with methanol under reflux, and the resulting methanol containing the polymer as swollen was placed into cold methanol. The white polymer separating out was isolated by filtration and dried at a reduced pressure, affording 7.0 g of white polymer. The polymer was sparingly soluble in a majority of solvents. TLC, IR and $^1$H-NMR (hot DMSO-$d_6$) analyses revealed that the polymer was a crosslinked copolymer comprising TMLS-$C_6$, styrene and divinylbenzene. The quaternary ammonium content was found to be 1.25 millieq/g.

EXAMPLE 37

A white polymer (4.9 g) was prepared by repeating the same reaction and aftertreatment as in Example 23 with the exception of using 3.25 g (6 mmoles) of TMLA-$C_6$ in place of TMLS-$C_6$ and 40 mg of 2,2'-bis(N-phenylamidinyl)-2,2'-azopropane dihydrochloride in place of AIBN. TLC, IR and $^1$H-NMR analyses indicated that the white polymer was a copolymer of TMLA-$C_6$ and styrene. The copolymer was found to be 42,000 in Mn and 2.2 in polydispersity Mw/Mn by GPC analysis. Quantitative determination of the quaternary ammonium content by colloidal titration revealed that the copolymer was 0.5:99.5 in TMLA-$C_6$/styrene ratio.

EXAMPLE 38

A white polymer (5.2 g) was prepared by repeating the same reaction and aftertreatment as in Example 23 with the exception of using 3.33 g (6 mmoles) of TMLB-$C_6$ instead of TMLS-$C_6$ and 40 mg of 2,2'-bis(N-phenylamidinyl)-2,2'-azopropane dihydrochloride in place of AIBN. The polymer was found to be a copolymer of TMLB-$C_6$ and styrene by TLC, IR and $^1$H-NMR analyses. The copolymer was found to be 48,000 in Mn and 2.4 in polydispersity Mw/Mn by GPC analysis. Quantitative determination of the quaternary ammonium content by colloidal titration indicated that the TMLB-$C_6$/styrene ratio of the copolymer was 1:99.

EXAMPLE 39

A white polymer (4.4 g) was obtained by repeating the same reaction and aftertreatment as in Example 23 except to that TMLS-$C_6$ was replaced by 3.42 g (6 mmoles) of TMLK-$C_6$. The polymer was found to be a copolymer of TMLK-$C_6$ and styrene by TLC, IR and $^1$H-NMR analyses. Similarly, the copolymer was found to be 101,000 in Mn, 1.8 in polydispersity Mw/Mn and 5:95 in TMLK-$C_6$/styrene ratio.

EXAMPLE 40

A white polymer (4.6 g) was obtained by repeating the same reaction and aftertreatment as in Example 23 except that TMLS-$C_6$ was replaced by 4.22 g (6 mmoles) of TMLC-$C_6$. The polymer was found to be a copolymer of TMLC-$C_6$ and styrene by TLC, IR and $^1$H-NMR analyses. The copolymer was found to be 90,000 in Mn, 1.7 in polydispersity Mw/Mn and 6:94 in TMLC-$C_6$/styrene ratio similarly by GPC analysis and colloidal titration.

EXAMPLE 41

A white polymer (7.0 g) was obtained by repeating the same reaction and aftertreatment as in Example 23 except that TMLS-$C_6$ was replaced by 3.78 g (6 mmoles) of TELV-$C_6$. TLC, IR and $^1$H-NMR analyses revealed that the polymer was a copolymer of TELV-$C_6$ and styrene. The copolymer was found to be 40,000 in Mn, 1.9 in polydispersity Mw/Mn and 12:88 in TELV-$C_6$/styrene ratio.

COMPARATIVE EXAMPLE 1

To carry out a reaction for preparing a copolymer from styrene (abbreviated as "ST") and 4-chloromethylstyrene (abbreviated as "CS") by the usual solution polymerization process, 77.0 g (0.74 mole) of styrene was reacted with 9.2 g (0.06 mole) of 4-chloromethylstyrene in 40 ml tetrahydrofuran in the presence of 0.66 g (4 mmoles) of AIBN at 60° C. for 20 hours. The mixture was placed into THF/methanol, followed by reprecipitation for purification, then by isolation through filtration and thereafter by drying in a vacuum to obtain 73.3 g of a white powdery polymer (abbreviated as "PCS"). The polymer was found to be a two-component copolymer, for example, by TLC, $^1$H-NMR and GPC analyses.

Total halogen quantitative analysis by the oxygen flask combustion method and elementary analysis revealed that the PCS was 91.7:8.3 in ST/CS molar ratio.

GPC determination (calculated as polystyrene) with use of THF as a solvent indicated that the PCS was 134,000 in number average molecular weight Mn and 1.57 in polydispersity Mw/Mn.

Next, 19.6 g of the PCS thus prepared was dissolved in 500 ml of THF, 7.07 g (18 mmoles) of the TML-$C_4$ obtained in Example 1 was added to the solution, and the mixture was reacted at 80° C. for 21 hours. The reaction mixture was cooled to room temperature and then placed into water. The resulting precipitate was filtered oil and dried, giving a white polymer. The polymer was dissolved in water, followed by reprecipitation from water twice for purification and then by drying to obtain 23.4 g of a white powdery polymer. The polymer was found to be the desired product comprising PCS having TML-$C_4$ introduced therein, for example, by TLC and $^1$HNMR analyses.

The polymer was checked by the oxygen flask combustion method for total halogen quantitative determination, by the silver nitrate titration method for ionic halogen quantitative determination, by elementary analysis for the determination of N % and by the colloidal titration method for the quantitative determination of quaternaly ammonium content to calculate the content of ST units, the content of remaining chloromethyl groups, i.e., of CS units and the amount of TML-$C_4$ units supported. The calculated values were 91.7 mole %, 0.5 mole % and 7.8 mole %, respectively.

Comparative Test Example 1

The polymers obtained in Example 25 and Comparative Example 1 were each placed into a glass container, then allowed to stand in a constant temperature bath adjusted to 50° C. and shielded from light, and thereafter checked for changes with time. One week later, no change was found in the polymer of Example 25, whereas the polymer of Comparative Example 1 was found slightly yellowed, with evolution of acid gas which turned pH test paper red. Twenty days later, the polymer of Example 25 was found unchanged in appearance and satisfactory in solubility in methanol, while a major or portion of the polymer of Comparative Example 1 was found degraded to a substance which was insoluble in methanol.

TEST EXAMPLE 1

Preparation of antibacterial fabric

For use as a test compound, the compound prepared in Example 23 was dissolved in methanol to obtain 0.1, 0.2 and 0.5 wt. % methanol solutions. Next cotton shirting, JIS standard fabric (hereinafter referred to as the "fabric"), was dipped in the methanol solution for padding. Next, the fabric was immediately checked for weight and thereafter cured at 105° C. for 30 minutes to completely fix the test compound to the fabric. The fabric was used as an "antibacterial fabric" for the following test.

The weight (mg/g fabric) of test compound fixed to the antibacterial fabric is expressed by the following equation (1):

$$C=(B-A)(W/100)(1/A)(1000) \quad (I)$$

A: initial weight. (g/predetermined area) of the fabric
B: weight (g/predetermined area) of the fabric immediately before curing
C: weight (mg/g fabric) of test compound fixed to the antibacterial fabric
W: concentration (wt. %) of the methanol solution of test compound From Equation (1), the following relationship was established between the value W and the value C.

| W (concn. of methanol soln. of test compound) (wt. %) | C (wt. of test compound fixed to fabric) (mg/g fabric) |
|---|---|
| 0.1 | 1.0 |
| 0.2 | 2.0 |
| 0.5 | 5.0 |

Antibacterial Test

The "antibacterial fabric" thus obtained was tested according to The Society for Antibacterial and Antifungal Agents, Japan, "Method of Testing Textile Products Subjected to Antibacterial Treatment for Inhibition of Growth of Bacteria" (hereinafter referred to as the "antibacterial textile test method"). The strains of test bacteria are those prescribed for the method plus *Pseudomonas aeruginosa* ATCC 10145. Thus, five strains were used which were *Staphylococcus aureus* FDA 209P, *Bacillus subtilis* ATCC 6633, *Klebsiella pneumoniae* ATCC 4352, *Escherichia coli* IFO 3301 and *Pseudomonas aeruginosa* ATCC 10145. As to the method of counting the number of live cells, reference was made to "Antibacterial and Antimold Handbook," edited by The Society for Antibacterial and Antifungal Agents, Japan, 1986, pp.678–691.

Expression of Results

The test results were expressed following the procedure described below. The bactericidal index was given by Equation (II).

$$Bactericidal\ index=log\ N(I)-log\ N(D) \quad (II)$$

$$Bactericidal\ index=log\ N(I)-log\ N(D) \quad (II)$$

wherein N(I) is the initial number of cells, and N(D) is the number of cells in the group to which the chemical agent (specimen) was added.

Next, such bactericidal indices were expressed according to the following four criteria of:

| Bactericidal index of less than 1 | ... 1 |
|---|---|
| Bactericidal index of at least 1 to less than 2 | ... 2 |
| Bactericidal index of at least 2 to less than 3 | ... 3 |
| Bactericidal index of at least 3 | ... 4 |

Table 4 shows the results.

TABLE 4

| | Bactericidal Test: weight (mg/g fabric) of Test Compound Fixed to "Antibacterial Fabric" | | | | |
|---|---|---|---|---|---|
| weight | S. aureus FDA 209P | B. subtilis ATCC 6633A | K. pneumoniae ATCC 4352 | E. coli IFO 3301 | P. aeruginosa ATCC 10145 |
| 1.0 mg | 3 | 3 | 3 | 3 | 3 |
| 2.0 mg | 3 | 3 | 3 | 3 | 3 |
| 5.0 mg | 4 | 4 | 4 | 4 | 4 |

EXAMPLES 42 AND 43

The desired allyl ether derivatives were prepared by repeating substantially the same reaction and aftertreatment as in Example 22 except that TMLE-$C_6$ was replaced by 5.61 g (10 mmoles) of TMLP-$C_6$ obtained in Example 19 or by 6.70 g (10 mmoles) of TMLB-$C_6$ obtained in Example 20. Table 5 shows the results.

TABLE 5

| Ex. | Compound (12) (solvent) | Compound (13) | Compound (1b) | Yield (%) |
|---|---|---|---|---|
| 42 | TMLP-$C_6$ (dichloromethane) | CH$_2$=CH−CH$_2$−Br | CH$_2$=CH−CH$_2$O−(CH$_2$)$_3$−N$^+$(CH$_3$)$_2$−(CH$_2$)$_6$−N$^+$(CH$_3$)$_2$−C$_{12}$H$_{25}$ .2Br$^-$ (TML3A-$C_6$) | 74 |
| 43 | TMLP-$C_6$ (dichloromethane) | CH$_2$=CH−CH$_2$−Br | CH$_2$=CH−CH$_2$O−(CH$_2$)$_4$−N$^+$(CH$_3$)$_2$−(CH$_2$)$_6$−N$^+$(CH$_3$)$_2$−C$_{12}$H$_{25}$ .Br$^-$.OTs$^-$ (TML4A-$C_6$) | 70 |

EXAMPLES 44 TO 46

The same reaction and aftertreatment as in Example 37 were repeated with the exception of using 9.05 g (15 mmoles) of TML2A-$C_6$ obtained in Example 22, 9.30 g (15 mmoles) of TML3A-$C_6$ obtained in Example 42 or 10.8 g (15 mmoles) of TML4A-$C_6$ obtained in Example 43, in place of TMLA-$C_6$, whereby 4.9 g, 5.0 g and 5.4 g of white powdery polymers were obtained, respectively. TLC, IR and $^1$H-NMR analyses revealed that these polymers were copolymers of styrene, and TML2A-$C_6$ (Example 44) or TML3A-$C_6$ (Example 45) or TML4A-$C_6$ (Example 46). The polymer obtained in Example 44 was 78,000 in Mn and 3.6 in polydispersity Mw/Mn, the polymer obtained in Example 45 was 83,000 in Mn and 4.1 in polydispersity Mw/Mn, and the polymer obtained in Example 46 was 101,000 in Mn and 2.9 in polydispersity Mw/Mn, as determined by GPC analysis. Quantitative determination of the quaternary ammonium content by colloidal titration revealed that the copolymers were composed of TML2A-$C_6$, TML3A-$C_6$ or TML4A-$C_6$, and styrene in the ratio of 4.0:96.0, 2.8:97.2 or 4.5:95.5, respectively.

EXAMPLES 47 TO 49

Preparation of antibacterial fabric

The compounds prepared in Examples 23, 40 and 45 were used in Examples 47 to 49, respectively, as test compounds. Each of these compounds was dissolved in methanol to obtain 0.1, 0.2 and 0.5 wt. % methanol solutions. Next, cotton shirting, JIS standard fabric (hereinafter referred to as the "fabric"), was dipped in the methanol solution for padding. Next, the fabric was immediately checked for weight and thereafter cured at 105° C. for 30 minutes to completely fix the test compound to the fabric. The fabric was used as an "antibacterial fabric" for the following test.

The weight (mg/g fabric) of test compound fixed to the antibacterial fabric is expressed by the foregoing equation (I):

$$C=(B-A)(W/100)(1/A)(1000) \qquad (I)$$

A: initial weight (g/predetermined area) of the fabric
B: weight (g/predetermined area) of the fabric immediately before curing
C: weight (mg/g fabric) of test compound fixed to the antibacterial fabric
W: concentration (wt. %) of the methanol solution of test compound From Equation (I), the following relationship was established between the value W and the value C.

| Ex. | W (concn. of methanol soln. of test compound) (wt. %) | C (wt. of test compound fixed to fabric) (mg/g fabric) |
|---|---|---|
| 47 | 0.1 | 1.0 |
|  | 0.2 | 2.0 |
|  | 0.5 | 5.0 |
| 48 | 0.1 | 1.0 |
|  | 0.2 | 2.1 |
|  | 0.5 | 5.3 |
| 49 | 0.1 | 1.1 |
|  | 0.2 | 2.2 |
|  | 0.5 | 5.3 |

TEST EXAMPLE 2 (ANTIBACTERIAL TEST)

The "antibacterial fabric" thus obtained was tested according to The Society for Antibacterial and Antifungal Agents, Japan, "Method of Testing Textile Products Subjected to Antibacterial Treatment for Inhibition of Growth of Bacteria" (hereinafter referred to as the "antibacterial textile test method"). The strains of test bacteria are those prescribed for the method plus *Pseudomonas aeruginosa* ATCC 10145. Thus, five strains were used which were *Staphylococcus aureus* FDA 209P, *Bacillus subtills* ATCC 6633, *Klebsiella pneumoniae* ATCC 4352, *Escherichia coli* IFO 3301 and *Pseudomonas aeruginosa* ATCC 10145. As to the method of counting the number of live cells, reference was made to "Antibacterial and Antimold Handbook," edited by The Society for Antibacterial and Antifungal Agents, Japan, 1986, pp.678–691.

Expression of Results

The test results were expressed following the procedure described below. The bactericidal index was given by Equation (II).

$$\text{Bactericidal index} = \log N(I) - \log N(D) \quad \text{(II)}$$

wherein N(I) is the initial number of cells, and N(D) is the number of cells in the group to which the chemical agent (specimen) was added.

Next, such bactericidal indices were expressed according to the following tour criteria of:

| | |
|---|---|
| Bactericidal index of less than 1 | ...1 |
| Bactericidal index of at least 1 to less than 2 | ...2 |
| Bactericidal index of at least 2 to less than 3 | ...3 |
| Bactericidal index of at least 3 | ...4 |

Table 6 shows the results.

TABLE 6

Bactericidal Test: weight (mg/g fabric) of Test Compound Fixed to "Antibacterial Fabric" and antibacterial effect

| Ex. | weight | S. aureus FDA 209P | B. subtilis ATCC 6633A |
|---|---|---|---|
| 47 | 1.0 mg | 3 | 3 |
|  | 2.0 mg | 3 | 3 |
|  | 5.0 mg | 4 | 4 |
| 48 | 1.0 mg | 3 | 3 |
|  | 2.1 mg | 3 | 3 |
|  | 5.3 mg | 4 | 4 |
| 49 | 1.1 mg | 3 | 3 |
|  | 2.2 mg | 3 | 3 |
|  | 5.3 mg | 4 | 4 |

| Ex. | weight | K. pneumoniae ATCC 4352 | E. coli IFO 3301 | P. aeruginosa ATCC 10145 |
|---|---|---|---|---|
| 47 | 1.0 mg | 3 | 3 | 3 |
|  | 2.0 mg | 3 | 3 | 3 |
|  | 5.0 mg | 4 | 4 | 4 |
| 48 | 1.0 mg | 3 | 3 | 3 |
|  | 2.1 mg | 3 | 3 | 3 |
|  | 5.3 mg | 4 | 4 | 4 |
| 49 | 1.1 mg | 3 | 3 | 3 |
|  | 2.2 mg | 3 | 3 | 3 |
|  | 5.3 mg | 4 | 4 | 4 |

COMPARATIVE EXAMPLE 2

4-Chloromethylstyrene was subjected to suspension polymerization in the usual manner to obtain a homopolymer (PCS-H). The polymer obtained was washed with hot acetone to remove the unreacted monomer.

TML-$C_6$ (56 g) obtained in Example 3 was reacted with 53.0 g of PCS-H in 850 ml of THF solvent at 65° C. for 64 hours, consequently affording 96.0 g of a yellow powdery polymer (yield 88.1%).

TEST EXAMPLE 3 (ACUTE SKIN IRRITATION)

The polymer obtained in Example 23, Example 40, Example 45 or Comparative Example 2 was tested for acute skin irritation according to OECD Chemicals Test Guideline 2 (edited by Foundation of Chemicals Inspection Association), 404.

A powder of the compound was applied to a small portion of the skin of a rabbit and covered with a gauze patch as fixed with a tape. Four hours later, the patch was removed, and the skin was then checked. Table 7 shows the results.

In Table 7:

| | |
|---|---|
| 0: no erythema | 0: no edema |
| 1: very slight erythema | 1: very slight edema |
| 2: distinct erythema | 2: slight edema |
| 3: medium to intense erythema | 3: medium edema |
| 4: intense erythema | 4: intense edema |

TABLE 7

| | | Time after removing patch | | | |
|---|---|---|---|---|---|
| | | 1 hour | 24 hours | 48 hours | 72 hours |
| Ex. 23 | erythema | 0 | 0 | 0 | 0 |
|  | edema | 0 | 0 | 0 | 0 |
| Ex. 40 | erythema | 0 | 0 | 0 | 0 |
|  | edema | 0 | 0 | 0 | 0 |
| Ex. 45 | erythema | 0 | 0 | 0 | 0 |
|  | edema | 0 | 0 | 0 | 0 |
| Com. Ex. 2 | erythema | 2 | 1 | 0 | 0 |
|  | edema | 1 | 0 | 0 | 0 |

EXAMPLES 50 TO 52

A 0.5 g quantity of each of the polymers obtained in Examples 23, 40 and 43 was dissolved in 100 g of methanol. A cut piece of high-density polyethylene film (HDPE, 80 μm in thickness), measuring 14 cm×50 cm, was immersed in each of the three kinds of methanol solutions for 30 seconds, then withdrawn and dried at 25° C. for 1 hour, followed by further drying in a dryer at 50° C. for 1 hour. The film pieces thus prepared are referred to as Examples 50, 51 and 52.

The amount of polymer deposited on the film surface was 0.1 μmol/cm$^2$.

COMPARATIVE EXAMPLES 3 AND 4

Polyurethane resin (0.2 g), 30 g of methyl ethyl ketone, 70 g of toluene and 0.2 g of benzalkonium chloride (product of NAKALAI TESQUE INC.) were mixed together to prepare a solution, in which the same HDPE film piece as used for Example 50 was immersed, followed by the same treatment as above to prepare Comparative Example 3.

Comparative Example 4 was prepared in the same manner as in Example 11 except that the benzalkonium chloride was replaced by 1,6-di(N-p-chlorophenylbiguanide)-hexanedigluconate.

TEST EXAMPLES 4 (ADHESION TO FILM)

Each of the HDPE film pieces of Examples 50 to 52 and Comparative Examples 3 and 4 was placed into a 2-liter beaker along with 1 liter of distilled water, followed by vigorous stirring at 25° C. for 8 hours for a separation test. The film was withdrawn, dried at 25° C. for 1 hour, thereafter treated with 10$^{-4}$M Bromophenol Blue (phosphoric acid buffer pH 7.0) to develop a blue color over the surface and checked for separation or release of the high polymer compound coating to determine a change in the adhesion to the film due to the separation test. Table 8 shows the result.

In Table 8, a uniformly colored sample is represented by o, and a locally unevenly colored sample by Δ.

TABLE 8

| | before separation test | after separation test |
|---|---|---|
| Ex. 50 | O | O |
| Ex. 51 | O | O |
| Ex. 52 | O | O |
| Com. Ex. 3 | O | Δ |
| Com. Ex. 4 | O | Δ |

TEST EXAMPLE 5 (ANTIBACTERIAL TEST OF FILM)

The film pieces of Examples 50 to 52 and Comparative Examples 3 and 4 were partly tested for separation with saturated steam at 90° C. for 90 minutes and thereafter dried at 25° C. for 24 hours for use as samples for the following test after the separation test.

A cell culture incubated with shaking on a nutrient broth (Difco. Lab.) for 18 hours was diluted with aseptic water to 10$^4$ cells/ml. Film pieces (Examples 11 to 20, Comparative Examples 2 and 3) cut out before and after the separation test were placed into a gas barrier bag of polypropylene (180×80 cm) along with 50 ml of the diluted culture, and the bag was heat sealed. The bag containing the film pieces was set in a constant-temperature shaking culture device at 37° C. and tested for 18 hours.

After the incubation test, the resulting cell suspension was collected and checked for the number of remaining cells by the usual colony counting method. The following nine strains were used as test bacteria.

| No. | | |
|---|---|---|
| 1. | *Pseudomonas aeruginosa* | resistant isolate |
| 2. | *Klebsiella pneumoniae* | resistant isolate |
| 3. | *Escherichia coli* | resistant isolate |
| 4. | *Staphylococcus aureus* | resistant isolate a |
| 5. | *Staphylococcus aureus* | resistant isolate b |
| 6. | *Staphylococcus aureus* | resistant isolate c |
| 7. | *Staphylococcus aureus* | resistant isolate d |
| 8. | *Staphylococcus aureus* | resistant isolate e |
| 9. | *Bacillus subtilis* | resistant isolate |

Live cell counts of at least 10$^5$ cells/ml are represented by X, those of 10$^3$~10$^4$ cells/ml by Δ, those of 10~10$^2$ cells/ml by o, and zero by ⊙. Table 9 shows the results. The test strains listed in Table 9 were each represented only by the corresponding number given above.

TABLE 9

Antibacterial test of film (number of live cells) before separation test

| | Test strain No. | | | | | | | | |
|---|---|---|---|---|---|---|---|---|---|
| | 1 | 2 | 3 | 4 | 5 | 6 | 7 | 8 | 9 |
| Ex. 50 | ⊙ | ⊙ | ⊙ | ⊙ | ⊙ | ⊙ | ⊙ | ⊙ | ⊙ |
| Ex. 51 | ⊙ | ⊙ | ⊙ | ⊙ | ⊙ | ⊙ | ⊙ | ⊙ | ⊙ |
| Ex. 52 | ⊙ | ⊙ | ⊙ | ⊙ | ⊙ | ⊙ | ⊙ | ⊙ | ⊙ |
| Com. Ex. 3 | O | O | O | O | O | O | O | O | O |
| Com. Ex. 4 | O | O | O | O | O | O | O | O | O |
| Ex. 50 | O | ⊙ | O | ⊙ | ⊙ | ⊙ | ⊙ | ⊙ | ⊙ |
| Ex. 51 | O | ⊙ | O | ⊙ | ⊙ | ⊙ | ⊙ | ⊙ | ⊙ |
| Ex. 52 | O | ⊙ | O | ⊙ | ⊙ | ⊙ | ⊙ | ⊙ | ⊙ |
| Com. Ex. 3 | Δ | Δ | Δ | Δ | Δ | Δ | Δ | Δ | Δ |
| Com. Ex. 4 | Δ | Δ | Δ | Δ | Δ | Δ | Δ | Δ | Δ |

EXAMPLES 53 TO 55

Each of the polymers obtained in Examples 23, 40 and 45 was made into 0.5 wt. % methanol solution, in which a fabric (cotton shirting, JIS standard fabric) was immersed and treated by the exhaustion method for use in an antibacterial test. The concentration of the polymer applied to the fabric was so adjusted that the amount of active groups of the polymer supported thereon would be 5 μmoles/g fabric. Thus, Examples 53, 54 and 55 were prepared.

COMPARATIVE EXAMPLE 5

Benzalkonium chloride (BAG) was dissolved in a resin emulsion to a concentration of 0.5 wt. % and then applied to the same fabric as used for Example 53. The fabric was dried at 50° C. for 12 hours and thereafter subjected to an antibacterial test. The concentration of BAG applied to the fabric was adjusted to 5 μmoles/g fabric.

TEST EXAMPLE 6 (ANTIBACTERIAL TEST OF FABRIC)

Each of the fabrics of Examples 53 to 55 and Comparative Example 5 was subjected to a bacterial growth inhibition test to calculate the sterilization efficiency, without laundering or after having been laundered a specified number of times.

In each of the laundering cycles, the fabric was laundered at a water temperature of 40° C. in a bath ratio of 1:30 for 5 minutes using a household electric washing machine and "NISSAN NONION NS-210" (product of Nippon Oils & Fats Co., Ltd.) as a detergent in an amount of 0.5 g per liter of water, and thereafter washed with water for 5 minutes while allowing water to overflow the machine.

The bacterial growth inhibition test was conducted by the following method using the same nine strains as in Test Example 4 as test bacteria. According to a JIS test method (to be incorporated into JIS in 1993), the test fabric (0.2 g) was placed into aseptic bile and autoclaved at 121° C. for 15 minutes for sterilization. The strain was incubated with shaking on NB medium at 37° C. for 18 hours, and the culture was diluted with 1/1NB to about 10⁶ cells/ml. The bile was inoculated with 0.1 ml oi the cell suspension, followed by incubation at 37° C. for 18 hours. After the incubation, 10 ml of physiological saline containing 0.2% Tween 80 was added to the bile, and the mixture was shaken to wash out the resulting cells. The number of live cells was determined by the usual colony counting method. The test result is expressed in the same manner as in Test Example 4. Table 10 shows the result.

TABLE 10

Antibacterial test of fabric (number of live cells)

| | Test strain No. | | | | | | | | |
|---|---|---|---|---|---|---|---|---|---|
| | 1 | 2 | 3 | 4 | 5 | 6 | 7 | 8 | 9 |
| Laundering 0 cycle | | | | | | | | | |
| Ex. 53 | ○ | ⊚ | ○ | ⊚ | ⊚ | ⊚ | ⊚ | ⊚ | ⊚ |
| Ex. 54 | ⊚ | ⊚ | ⊚ | ⊚ | ⊚ | ⊚ | ⊚ | ⊚ | ⊚ |
| Ex. 55 | ⊚ | ⊚ | ⊚ | ⊚ | ⊚ | ⊚ | ⊚ | ⊚ | ⊚ |
| Com. Ex. 5 | ○ | ○ | ○ | ○ | ○ | ○ | ○ | ○ | ○ |
| Laundering 10 cycles | | | | | | | | | |
| Ex. 53 | ○ | ⊚ | ○ | ⊚ | ⊚ | ⊚ | ⊚ | ⊚ | ⊚ |
| Ex. 54 | ⊚ | ⊚ | ⊚ | ⊚ | ⊚ | ⊚ | ⊚ | ⊚ | ⊚ |
| Ex. 55 | ⊚ | ⊚ | ⊚ | ⊚ | ⊚ | ⊚ | ⊚ | ⊚ | ⊚ |
| Com. Ex. 5 | X | X | X | X | X | X | X | X | X |

(Industrial applicability)

The present invention provides a polymerizable monomer for readily giving an antibacterial polymer which is excellent in bactericidal activity, high in safety and stability and capable of retaining its effect for a prolonged period of time even in a reactive environment, and provides the polymer thereof.

We claim:

1. A polymerizable monomer represented by the general formula (1)

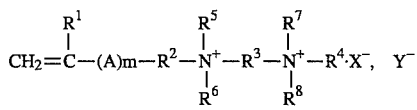

wherein $R^1$ is a hydrogen atom, methyl, chlorine or cyano, $R^2$ is alkylene having 1 to 4 carbon atoms, $R^3$ is alkylene having 3 to 10 carbon atoms, $R^4$ is alkyl having 6 to 18 carbon atoms, $R^5$ to $R^8$ are the same or different and are each alkyl or substituted alkyl having 1 to 3 carbon atoms, A is methylene, phenylene, substituted phenylene, —CH$_2$O—, —CH$_2$CH$_2$O—, —CO—, —CO—N(R$^9$)— (wherein R$^9$ is a hydrogen atom or methyl) or vinylene, m is 0 or 1, and X and Y are the same or different, and are each a monovalent anion or form a bivalent anion when taken together.

2. A polymer which has a structural unit derived from noncrosslinkable or crosslinkable vinyl monomer or from a mixture of such monomers, and a structural unit represented by the general formula (2)

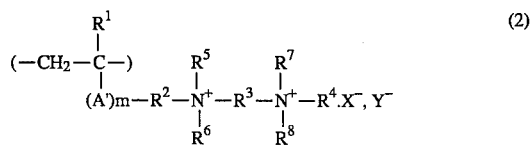

wherein $R^1$ is a hydrogen atom, methyl, chlorine or cyano, $R^2$ is alkylene having 1 to 4 carbon atoms, $R^3$ is alkylene having 3 to 10 carbon atoms, $R^4$ is alkyl having 6 to 18 carbon atoms, $R^5$ to $R^6$ are the same or different and are each alkyl or substituted alkyl having to 1 to 3 carbon atoms, A' is methylene, —CH$_2$O—, —CH$_2$CH$_2$O—, —CO—, —CO—N(R$^9$)— (wherein R$^9$ is a hydrogen atom or methyl) or vinylene, m is 0 or 1, and X and Y are the same or different, and are each a monovalent anion or form a bivalent anion when taken together.

3. A process for preparing a polymer characterized by polymerizing a noncrosslinkable or crosslinkable vinyl monomer or a mixture of such monomers with a monomer represented by the general formula (1).

4. A disinfectant composition comprising a polymer for destroying bacteria which are resistant to antibiotics, said polymer having a structural unit derived from the general formula (2)

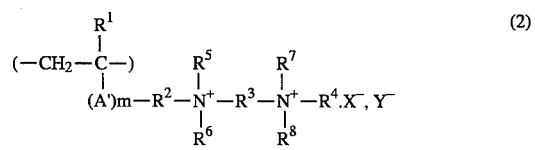

wherein $R^1$ is a hydrogen atom, methyl, chlorine or cyano, $R^2$ is alkylene having 1 to 4 carbon atoms, $R^3$ is alkylene having 3 to 10 carbon atoms, $R^4$ is alkyl having 6 to 18 carbon atoms, $R^5$ to $R^8$ are the same or different and are each alkyl or substituted alkyl having 1 to 3 carbon atoms, A' is methylene, —CH$_2$O—, —CH$_2$CH$_2$O—, —CO—, —CO—N(R$^9$)— or vinylene, R$^9$ is a hydrogen atom or methyl, m is 0 or 1, and X and Y are the same or different, and are each a monovalent anion or form a bivalent anion when taken together.

5. A method of imparting antibacterial properties to fibers by applying to the fibers, a polymer having a structural unit derived from the general formula (2)

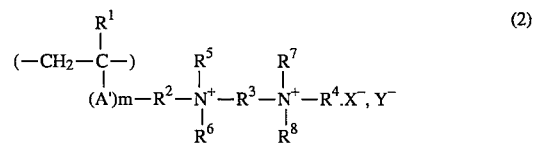

wherein $R^1$ is a hydrogen atom methyl, chlorine or cyano, $R^2$ is alkylene having 1 to 4 carbon atoms, $R^3$ is alkylene having 3 to 10 carbon atoms, $r^4$ is alkyl having 6 to 18 carbon atoms, $R^5$ to $R^8$ are the same or different and are each alkyl or substituted alkyl having 1 to 3 carbon atoms, A' is methylene, —CH$_2$O—, —CH$_2$CH$_2$O—, —CO—, —CO—N(R$^9$)— or vinylene, R$^9$ is a hydrogen atom or methyl, m is 0 or 1, and X and Y are the same or different, and are each a monovalent anion or form a bivalent anion when taken together.

* * * * *